United States Patent [19]

Pinchuk

[11] Patent Number: 5,019,090
[45] Date of Patent: May 28, 1991

[54] RADIALLY EXPANDABLE ENDOPROSTHESIS AND THE LIKE

[75] Inventor: Leonard Pinchuk, Miami, Fla.

[73] Assignee: Corvita Corporation, Miami, Fla.

[21] Appl. No.: 240,000

[22] Filed: Sep. 1, 1988

[51] Int. Cl.$^5$ .......................... A61N 29/02; A61F 2/06
[52] U.S. Cl. ........................................ 606/194; 606/1; 606/108; 623/1
[58] Field of Search ............... 128/341, 343, 344, 840, 128/325, 303 R; 623/1; 606/191, 194, 198, 1, 106, 108

[56] References Cited

U.S. PATENT DOCUMENTS

| | | |
|---|---|---|
| 2,701,559 | 2/1955 | Cooper . |
| 3,490,975 | 1/1970 | Lightwood et al. . |
| 3,635,215 | 1/1972 | Shea et al. ........................... 128/840 |
| 4,140,126 | 2/1979 | Choudhury . |
| 4,141,364 | 2/1979 | Schultze . |
| 4,425,908 | 1/1984 | Simon . |
| 4,503,569 | 3/1985 | Dotter . |
| 4,512,338 | 4/1985 | Balko et al. . |
| 4,553,545 | 11/1985 | Maass et al. . |
| 4,560,374 | 12/1985 | Hammerslag . |
| 4,580,568 | 4/1986 | Gianturco . |
| 4,597,389 | 7/1986 | Ibrahim et al. ................. 128/303 R |
| 4,649,922 | 3/1987 | Wiktor . |
| 4,655,771 | 4/1987 | Wallsten . |
| 4,665,918 | 5/1987 | Garza et al. . |
| 4,669,611 | 10/1987 | Bowden . |
| 4,681,110 | 7/1987 | Wiktor . |
| 4,693,721 | 9/1987 | Ducheyne . |
| 4,733,665 | 3/1988 | Palmaz . |
| 4,739,762 | 4/1988 | Palmaz . |
| 4,800,882 | 1/1989 | Gianturco ........................... 128/343 |
| 4,830,003 | 5/1989 | Wolff et al. ............................. 623/1 |
| 4,856,516 | 8/1989 | Hillstead ................................ 623/1 |
| 4,886,062 | 12/1989 | Wiktor ................................ 623/1 X |
| 4,969,458 | 11/1990 | Wiktor ................................ 606/108 |

FOREIGN PATENT DOCUMENTS

| | | |
|---|---|---|
| 0282175 | 9/1988 | European Pat. Off. . |
| 0312852 | 4/1989 | European Pat. Off. . |
| 0279885 | 8/1970 | U.S.S.R. ................................ 606/106 |
| 1205743 | 9/1970 | United Kingdom . |
| 2135585 | 9/1984 | United Kingdom . |

OTHER PUBLICATIONS

Palmaz et al, "Expandable Intraluminal Graft: A Preliminary Study," *Radiology*, 156:73-77, 1985.
Palmaz et al, "Expandable Intrahepatic Portacaval Shunt Stents: Early Experience in the Dog," *American Journal of Radiology*, 145:821-825, Oct., 1985.
Duprat et al, "Self-expanding Metallic Stents for Small Vessels: An Experimental Evaluation," *Radiology*, 162:469-472, 1987.
Lawrence et al, "Percutaneous Endovascular Graft: Experimental Evaluation", *Radiology*, 163:357-360, 1987.
Sigwart et al, "Intravascular Stents to Prevent Occlusion and Restenosis After Transluminal Angioplasty," *New England Journal of Medicine*, vol. 316, No. 12, Mar. 19, 1987.
Schatz et al, "Intravascular Stents for Angioplasty," *Cardio*, pp. 27-31, Dec., 1987.

*Primary Examiner*—Randall L. Green
*Assistant Examiner*—Stephanie L. Iantorno
*Attorney, Agent, or Firm*—Lockwood, Alex, FitzGibbon & Cummings

[57] ABSTRACT

Radially expandable endoprostheses or stents are provided, as well as their method of manufacture. These stents include a plurality of adjacent generally circumferential sections that are substantially axially positioned with respect to each other. At least one of the generally circumferential sections has a generally circumferentially disposed expandable segment that imparts circumferential and radial expandability to the stent.

20 Claims, 4 Drawing Sheets

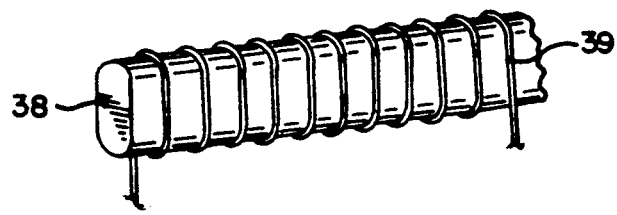
FIG_1_
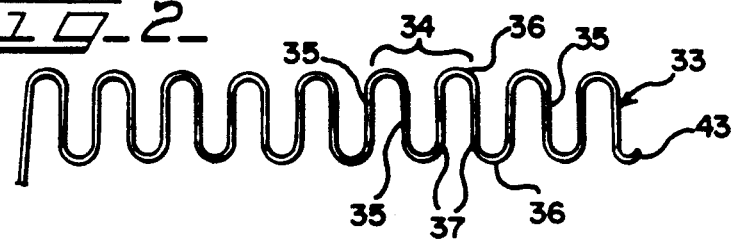
FIG_2_
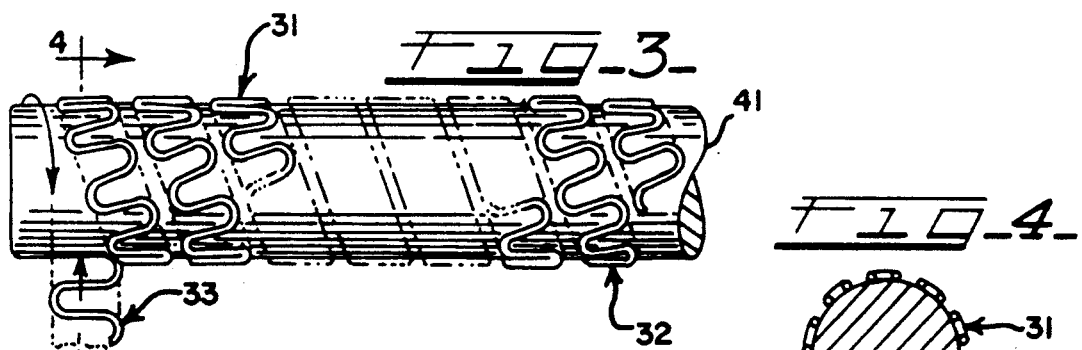
FIG_3_
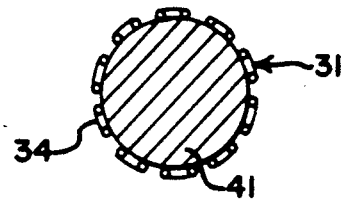
FIG_4_
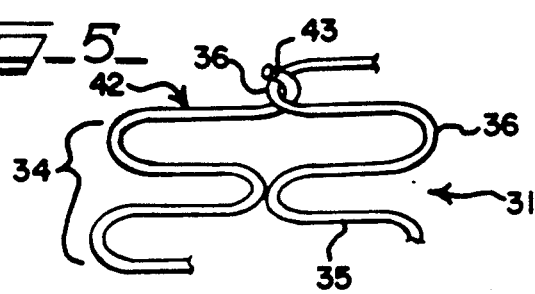
FIG_5_
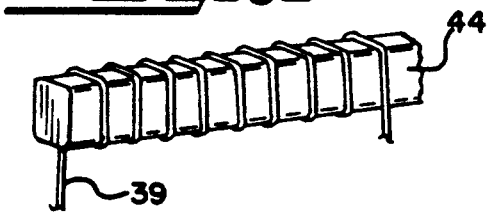
FIG_6_
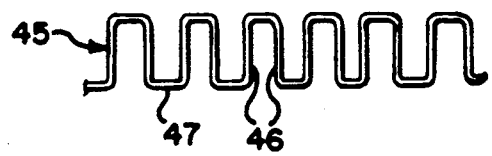
FIG_7_

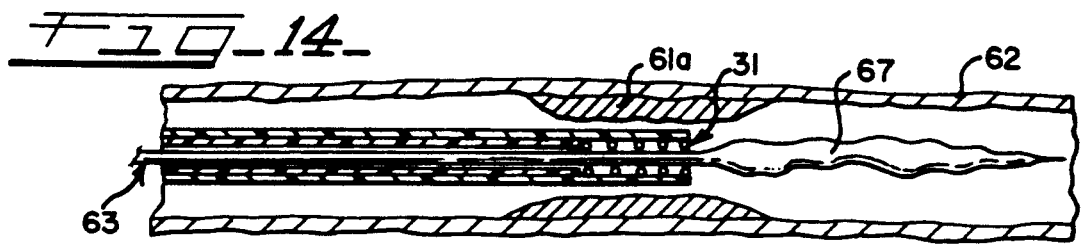
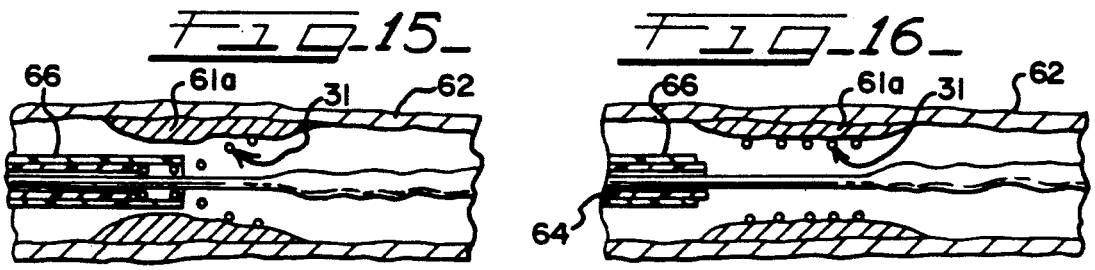
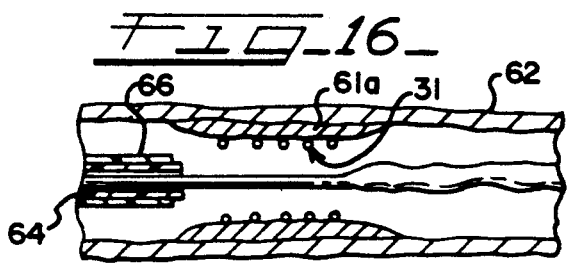
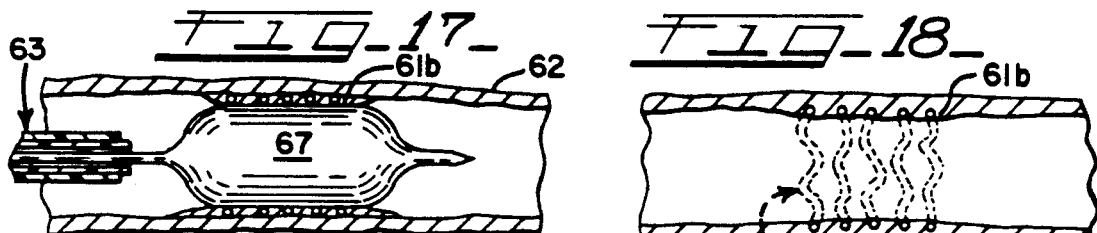
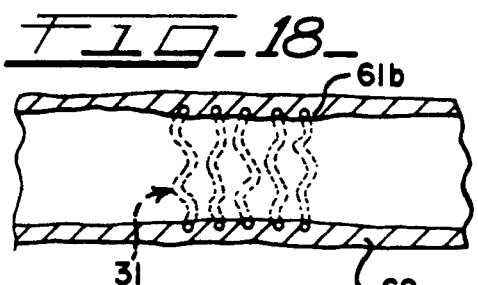
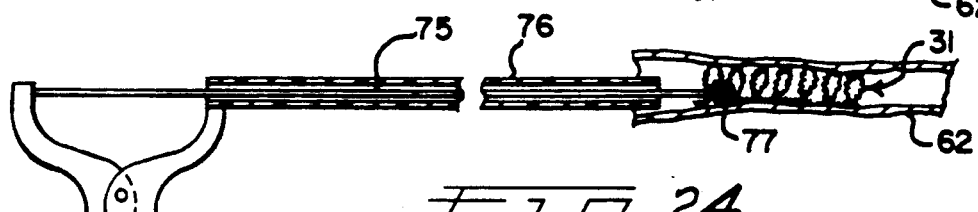
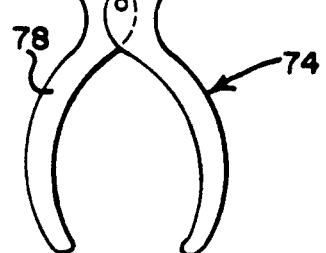
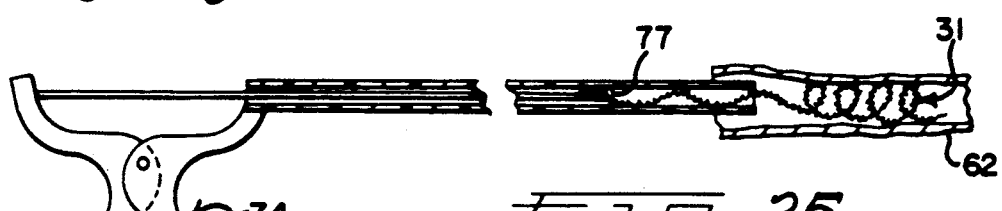
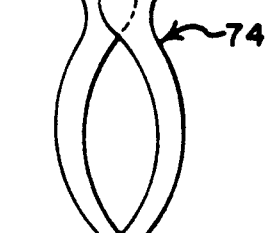

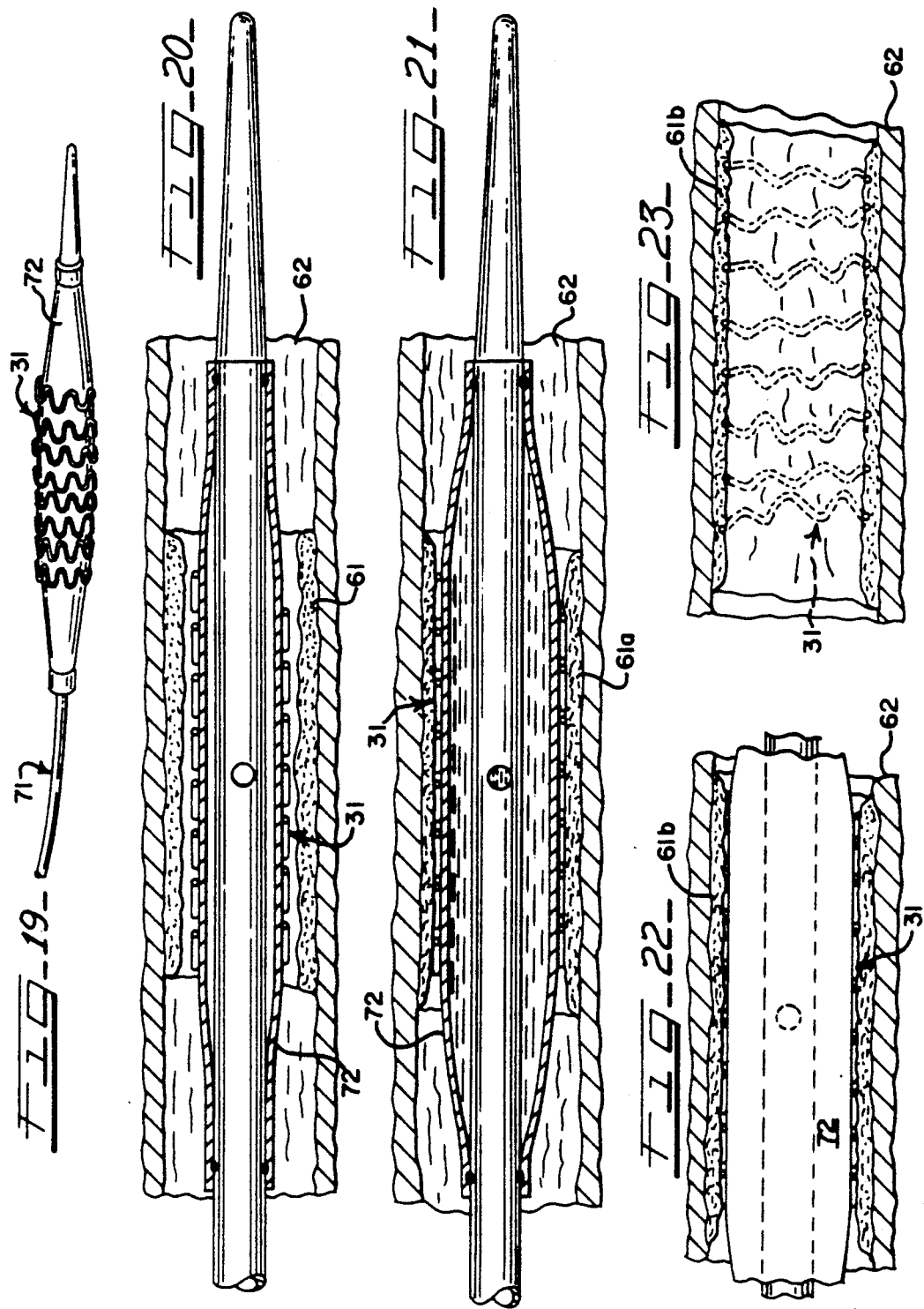

RADIALLY EXPANDABLE ENDOPROSTHESIS AND THE LIKE

BACKGROUND AND DESCRIPTION OF THE INVENTION

The present invention generally relates to endoprosthesis devices, to a procedure for making same, and to the use thereof. More particularly, the invention relates to a generally tubular endoprosthesis that is radially expandable between a generally unexpanded insertion circumference and an expanded implantation circumference which is greater than the unexpanded insertion circumference. Included are a plurality of generally circumferential sections, one or more of which includes one or more expandable segments that are bendable members which are generally collapsed when the endoprosthesis is in its generally unexpanded insertion orientation and which are generally opened when the endoprosthesis is in its expanded implantation orientation.

Endoprostheses are known for treating stenoses, stricture, aneurysm conditions and the like. An endoprosthesis device of this type, which is at times referred to as a stent, is typically placed or implanted by a mechanical transluminal procedure. Often a device of this type is percutaneously implanted within the vascular system to reinforce collapsing, partially occluded, weakened or abnormally dilated localized sections of a blood vessel or the like. Stents of this type can also be used in the urinary tract, the bile tract, the intestinal tract and the like. When endoprostheses or stents are used to treat a stenosis condition, typically such is done in association with a dilation element such as an angioplasty balloon. In this instance, the dilation element or balloon device opens the constriction, and a stent or the like is positioned thereat in order to prevent or at least substantially slow re-formation of the stenosis.

One attribute of a stent is that it is radially compressible and expandable so that it will easily pass through a blood vessel or the like when collapsed and will expand to its implanted size after the stenosis, aneurysm or the like has been reached. It is also desirable that a stent be generally flexible throughout its length so that it is easily maneuverable through bends and curves of the blood vessel or the like. It is typically desirable that a stent or endoprosthesis have a substantial amount of open space so as to allow for endothelialization along its length, to minimize the foreign body response, and to minimize interference with collateral blood vessels and the like. While it is important that a stent or endoprosthesis lodge securely into place at the desired location, it can be advantageous to have a stent that is removable through a transluminal percutaneous procedure, should removal be needed.

Various currently known stent products have structures that are essentially coiled springs. When this type of spring stent is tightly coiled, its diameter is relatively small for insertion through a blood vessel or the like. When the coil is sprung or coiled more loosely, the stent assumes its expanded, implantation orientation. Maass et al U.S. Pat. No. 4,553,545 is illustrative of this type of coiled spring stent or endoprosthesis. Multihelix or braided stents are also known. Stents of this general type suffer from poor maneuverability, and they are relatively thick walled and three dimensional. They are also difficult to remove once implanted, and they may exhibit numerous exposed, relatively sharp or jagged ends. Palmaz U.S. Pat. No. 4,733,665 is representative of an expandable stent of this general type. Gianturco U.S. Pat. No. 4,580,568 illustrates a percutaneous endovascular stent formed of stainless steel wire that is arranged in a closed zig-zag pattern somewhat in the nature of a bookbinder spring. Such a structure is somewhat unsymmetrical, and it may be subject to reocclusion due to the very large open space that is typically present between the wires of this type of device. Another type of stent is known as a Statz stent, and it includes a hypodermic tube with longitudinal slots etched into its body. While such a device has a high ratio of unexpanded to expanded diameter, it is a comparatively rigid, sharp-edged device which is difficult to maneuver through a tortuous path and is not easily removed in a transluminal manner.

With many of these currently known stent structures, the axial length of the stent decreases as the circumference of the stent increases, which is typically a disadvantage. For example, any such length reduction must be taken into consideration in selecting proper stent sizing for a particular implantation procedure. Also, this attribute of many prior stents requires the passage through the blood vessel or the like of a stent which is longer than the length actually needed for the implantation procedure being performed. This is a particularly difficult problem for procedures in which the stent must be passed through a pathway having twists or turns, especially for a stent structure that is not easily bendable.

The present invention avoids the various deficiencies of these types of prior art structures and provides important and advantageous features of endoprostheses or stents and the use thereof. In summary, the endoprosthesis of this invention includes a plurality of generally circumferential sections that are generally adjacent to one another along their respective opposing generally circumferential edges. At least one of these generally circumferential sections has an expandable segment that imparts radial expandability to the generally circumferential section. The expandable segment is a bendable, elbow-like member that is bendable between a generally collapsed or closed orientation and a generally opened orientation and is capable of assuming bending orientations between one that is fully closed and one that is fully opened. By this structure, the endoprosthesis or stent has an unexpanded insertion circumference and an expanded implantation circumference, which is greater than the insertion circumference. In addition, this variation in circumference is achieved without substantially changing the axial length of the endoprosthesis or stent. The stent is made by a procedure that is relatively uncomplicated, and, generally speaking, the stent can be transluminally explanted if necessary.

It is a general object of the present invention to provide an improved radially expandable, axially extending endoprosthesis of the type that can be transluminally implanted.

Another object of the present invention is to provide an improved endoprosthesis or stent that can be constructed to have very large radial expansion capabilities.

Another object of this invention is to provide an improved radially expandable axially extending endoprosthesis that is extremely maneuverable and capable of moving through a tortuous path.

Another object of the present invention is to provide an improved radially expandable axially extending endoprosthesis that can, if desired, be transluminally explanted by means of, for example, a snare lead or catheter.

Another object of the present invention is to provide an improved radially expandable axially extending endoprosthesis which includes members that can be spaced apart or pointed in a manner that enhances lodging of the endoprosthesis at its implanted site.

Another object of the present invention is to provide an improved axially extending endoprosthesis that can be constructed in order to be radially expandable by an expanding member or balloon of a catheter device and/or can be radially expandable due to spring-like properties of the endoprosthesis.

Another object of this invention is to provide an improved procedure for making an axially extending and/or generally tubular endoprosthesis that is radially expandable.

Another object of the present invention is to provide an improved procedure and system for transluminally explanting an axially extending radially expandable endoprosthesis or stent.

Another object of the present invention is to provide an improved radially expandable endoprosthesis that substantially avoids the presentation of any frayed edges and that generally maintains its axial length throughout various radial expansion positions.

These and other objects, features and advantages of this invention will be clearly understood through a consideration of the following detailed description

BRIEF DESCRIPTION OF THE DRAWINGS

In the course of this description, reference will be made to the attached drawings, wherein:

FIG. 1 is a perspective view illustrating an early step in the procedure of making an endoprosthesis according to the present invention;

FIG. 2 is an elevational view illustrating a step subsequent to that shown in FIG. 1;

FIG. 3 is an elevational view showing a manufacturing step subsequent to that of FIG. 2, while also illustrating a substantially completed endoprosthesis in accordance with the present invention;

FIG. 4 is a cross-sectional view along the line 4—4 of FIG. 3;

FIG. 5 is an enlarged detail view of a portion of one end of the endoprosthesis shown in FIG. 3;

FIG. 6 is a perspective view illustrating an early step in the procedure of making another embodiment of the endoprosthesis;

FIG. 7 is an elevational view illustrating a step subsequent to that shown in FIG. 6, while also illustrating the configuration of a portion of this endoprosthesis prior to its circumferential orientation;

FIG. 14 is a generally cross-sectional view illustrating an implantation step subsequent to that shown in FIG. 13;

FIG. 15 is a generally cross-sectional view illustrating an implantation step subsequent to that of FIG. 14;

FIG. 16 is a generally cross-sectional view illustrating an implantation step subsequent to that illustrated in FIG. 15;

FIG. 17 is a generally cross-sectional view of an implantation step subsequent to that illustrated in FIG. 16;

FIG. 18 is a generally cross-sectional view of an implanted stent or endoprosthesis in accordance with the present invention;

FIG. 19 is an elevational view of an endoprosthesis and distal end of a balloon catheter for an implantation procedure that is especially suitable for an endoprosthesis according to the present invention that is constructed of a malleable-type of material;

FIG. 20 is a generally cross-sectional illustration of the endoprosthesis and catheter of FIG. 19 positioned within a blood vessel;

FIG. 21 is a generally cross-sectional illustration of an implantation stage subsequent to that shown in FIG. 20;

FIG. 22 is a generally cross-sectional illustration of an implantation stage subsequent to that shown in FIG. 21;

FIG. 23 is a generally cross-sectional illustration of an implanted stent or endoprosthesis according to the present invention;

FIG. 24 is a generally cross-sectional illustration of a snare catheter shown explanting a stent or endoprosthesis in accordance with the present invention; and FIG. 25 is a generally cross-sectional illustration showing a further stage of the explantation procedure illustrated in FIG. 24.

DESCRIPTION OF THE PARTICULAR EMBODIMENTS

Figure 8:
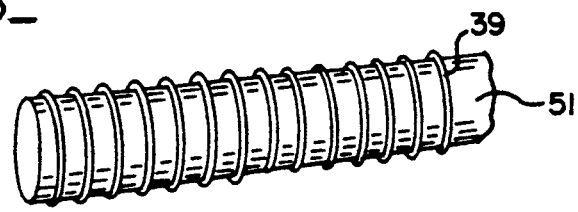
FIG. 8 is a perspective view illustrating an early step in the procedure of making a further embodiment of the endoprosthesis.

A radially expandable axially extending endoprosthesis or stent is generally designated as 31 in FIG. 3, as well as in FIG. 4. The stent includes a plurality of generally circumferential sections 32. In this illustrated embodiment, each of the circumferential sections 32 are formed from the same continuous, helically wrapped length, such as the undulating length 33 shown in FIG. 2.

At least one of the circumferential sections 32 includes at least one expandable segment 34. Expandable segment 34 is a bendable member that typically includes one or more legs 35. Each leg 35 is bendably secured to the rest of the circumferential section 32 by a so-called living joint or hinge that is a unitary or integral component of the leg 35 and the adjacent portion of the circumferential section 32. For example, in the embodiment illustrated in FIGS. 1 through 5, each leg 35 is bendably joined to another leg 35 through an integral or living hinge 36 which has a generally arcuate shape. When the stent 31 expands, the integral hinge 36 permits end portions 37 of the legs 35 to move farther apart, thereby increasing the circumference and diameter of the stent 31. Of course, the circumference and diameter of the stent 31 can be reduced by forces which move these end portions 37 closer to each other.

An understanding of the manner in which the endoprostheses according to this invention, such as the stent 31, can be made will be obtained from a consideration of FIGS. 1, 2 and 3. FIG. 1 shows a mandrel 38 that has a cross-sectional configuration that is somewhat oval in shape. Mandrel 38 can, for example, be a circular tube or rod that has been flattened on two opposing longitudinal portions in order to provide a cross-section that is generally rectangular in shape, with two opposing end portions thereof being arcuate or rounded. The mandrel is preferably composed of a malleable metal such as copper of the like.

A strand 39 of wire or other material, as generally discussed elsewhere herein, is generally tightly wound over the mandrel to the extent that the strand 39 takes on a cross-sectional shape along the lines of that of the mandrel 38. Preferably, this winding is done in a manner such that there is a substantial spacing between each individual wind of the strand 39. Generally speaking, the tighter the wind and the thinner the mandrel, the closer will be the spacing between the expandable segments 34 of the completed stent 31. After this winding has been completed, the wound strand 39 on the mandrel 38 is preferably heat annealed using a conventional annealing process for the type of wire used.

After this winding and annealing procedure has been completed, the mandrel 38 is removed from the wound strand 39. Removal of the wound strand is facilitated by axially stretching the malleable mandrel to effectively reduce its diameter. The wound strand 39 is then subjected to flattening forces so that the three-dimensional wound strand 39 is transformed into a generally planar shape such as that of the undulating length 33 shown in FIG. 2. These forces may be applied by any suitable means. For example, the wound strand 39 can be compressed between two planar surfaces, during which procedure, portions of the wound strand 39 are twisted until the generally uni-planar undulating length 33 is formed. This length has a generally sinusoidal character.

In order to complete formation of the stent 31 illustrated in FIG. 3, the undulating length 33 is then wound, in a generally helical manner, around a substantially cylindrical mandrel 41, as is generally illustrated in FIG. 3. This generally helical wrapping procedure continues until the desired number of circumferential sections are formed in order to provide a stent 31 of a desired length. It may, depending upon the type of wire used, be necessary to heat anneal the helical winding of FIG. 3.

With reference to FIG. 5, this winding procedure that is generally illustrated in FIG. 3 includes proceeding in a manner so as to avoid the presentation of any loose ends in the completed stent 31. This is readily accomplished by forming the strand 39 and the undulating length 33 so that each end circumferential section 42 has a free end 43 that readily hooks onto an adjacent portion of the stent 31, such as an integral hinge 36 of the circumferential section 32 that is adjacent to and inwardly spaced from the end circumferential section 42. The free end 43 illustrated in FIG. 5 is in the nature of a hook portion that readily loops or tucks into the integral hinge 36. It may be desirable in some embodiments to weld this hook to hinge 36.

Regarding the embodiment shown in FIGS. 6 and 7, the mandrel around which the strand 39 is wound is a substantially rectangular mandrel 44. As a result, the generally planar structure that is subsequently formed is an undulating length 45 that includes a plurality of legs 46 joined by a unitary or integral hinge or living hinge 47 that is typically less arcuate than the integral hinge 36. This undulating length 45 is then formed into an endoprosthesis or stent by helically winding same on a structure such as the cylindrical mandrel 41.

Figure 9:
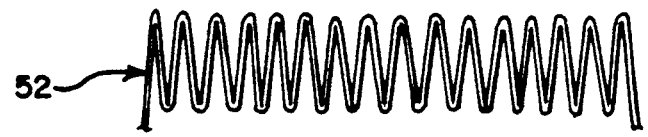
FIG. 9 is an elevational view illustrating a step subsequent to that shown in FIG. 8, while also illustrating the configuration of a portion of this endoprosthesis prior to its circumferential orientation.

Another embodiment of the endoprosthesis or stent is made in a manner generally illustrated in FIGS. 8 and 9. Here, the mandrel is a generally lens-shaped mandrel 51 which has a transverse cross-section that can be described as defining two convex surfaces positioned in back-to-back relationship with each other. Much in the same manner as the other embodiments, the elongated strand 39 is wound around the lens-shaped mandrel 51 and then preferably heat annealed. The mandrel 51 is subsequently moved therefrom, and the wound strand 39 is rendered substantially uni-planar in order to form undulating length 52 that is suitable for forming into a stent by wrapping around the mandrel 41.

Figure 10:
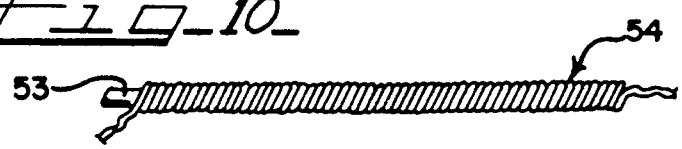
FIG. 10 is an elevational view of an early step in the manufacturing procedure for still a further embodiment of the endoprosthesis.
Figure 11:
FIG. 11 is an elevational view of a step subsequent to that shown in FIG. 10.
Figure 12:
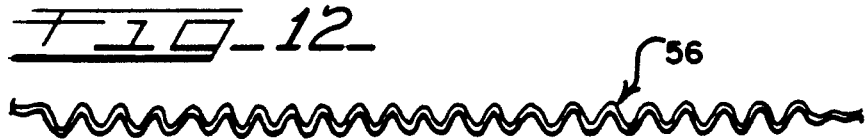
FIG. 12 is an elevational view of a manufacturing step subsequent to that illustrated in FIG. 11 and which shows a length of material suitable for winding on a mandrel in a generally helical manner in order to form the endoprosthesis of this embodiment.

Another embodiment illustrating the manufacture of an endoprosthesis or stent in accordance with this invention is generally illustrated in FIGS. 10, 11 and 12. A strand is wound around a small-diameter mandrel 53 which is circular in cross-section. In this case, the strand is formed into a tightly wound helix 54. Thereafter, the mandrel 53 is removed, and the strand is formed into a more loosely wound helix 55. For example, the helix 55 can be elongated such that the pitch angle is less than approximately 60°. This helix 55 is then flattened generally in the manner previously discussed, for example to 10 tons in a pneumatic press, in order to form a generally uni-planar undulating length 56. If desired, the length 56 can be axially compressed in a contained mold to the desired pitch angle. Length 56 is suitable for winding around cylindrical mandrel 41 in order to thereby form an endoprosthesis or stent.

Stents illustrated herein are typically capable of moving through a tortuous path that may be encountered in vascular system implantation. Such stents can be easily axially bent over a relatively small radius without damage or high bending resistance.

It should be appreciated that in the illustrated embodiments, each circumferential section 32 is generally identical. It is also possible within the spirit of the invention to provide circumferential sections that are not this uniformly shaped. For example, the circumference of adjacent sections can differ in order to form a stent that is not strictly shaped in the nature of a right cylinder. For example, tapered, truncated cone-shaped stents or stepped stents can be provided. In addition, in some applications, it can be suitable to include circumferential sections that are not composed entirely of expandable segments, but instead could include non-expandable portions that are joined by expandable segments. It also may be possible to provide stents within the spirit of the present invention which include one or more circumferential sections that form a stent device without proceeding with helical winding around cylindrical mandrel 41 or the like.

It is also possible to provide a stent that has a generally bifurcated structure for use in situations in which the stenosis, aneurysm or the like that is to be treated is at a branching location within the vascular system or the like. Such a bifurcated stent structure can be formed, for example, by joining portions of the opposing ends of two different unitary stents in order to provide a total structure that is bifurcated, Y-shaped or the like. It should also be appreciated that the stent can be composed of a plurality of helical strands in a parallel or antiparallel configuration.

The materials out of which stents according to the present invention can be made, and especially the expandable segments thereof, fall into two general categories. The material can be either elastic or generally inelastic. Examples of elastic materials include spring steels, stainless steel, Nitinol, Elgiloy, an alloy known as NP36N, and the like. Generally inelastic materials can be characterized as being malleable. Included are tantalum, titanium, silver, gold, and annealed versions of the elastic materials described herein. Polymers may also be used, such as polyether sulfone, polyimide, polycarbonate, polypropylene, ultra high molecular weight polyethylene, carbon fiber, Kevlar, and the like. It is also possible to coat these materials with porous or textured surfaces for cellular ingrowth and the like or with non-thrombogenic agents such as pyrolytic carbon, heparin, hydrogels, Teflon materials, silicones, polyurethanes and the like. The stents can be treated so that drugs can be eluted therefrom. It is also possible that certain stents may be made of biodegradable materials. In any event, the stent material, of course, is to be biocompatible. It should also be appreciated that the strand of stent material can be round in cross-section as is typical of wires, or it can be flat or rectangular in cross-section, for example.

Figure 13:
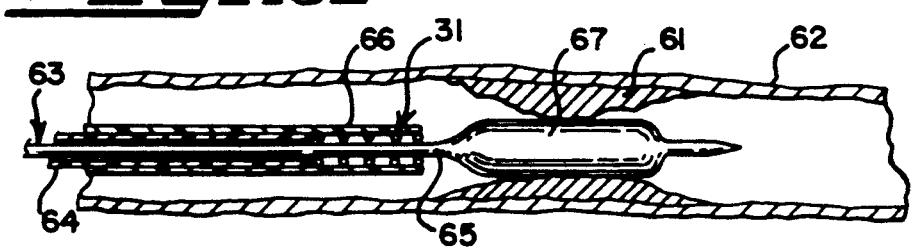
FIG. 13 is a generally cross-sectional view illustrating an early step in a procedure for implanting an endoprosthesis according to the present invention, this particular procedure being especially suitable for an endoprosthesis having spring-like properties.

FIGS. 13 through 18 illustrate an implantation procedure and an insertion system that is particularly suitable for stents that are constructed of an elastic material such as spring steel. A stenosis or lesion 61 is shown within a blood vessel 62. The stent 31 is positioned on a balloon catheter, generally designated as 63. An introducer tube or plunger 64, or a similar stop-providing structure, is positioned along the outside surface of the catheter tube 65. The stent 31 is located distally of the member 64, and a sheath 66 holds the stent 31 in a generally compressed state during which the expandable segments of the stent 31 are generally collapsed or closed. FIG. 13 further shows the balloon 67 of the catheter in a mode in which it is exerting outwardly radially directed forces on the lesions in order to dilate same to provide a wider opening as generally illustrated in FIG. 14 in order to thereby generally reduce the overall extent of the lesion to the general configuration of initially treated lesion 61a. At this time, the balloon 67 is collapsed, and the catheter 63 is moved in a distal direction so that the collapsed stent 31 is generally positioned within the lesion 61a. Next, as illustrated in FIG. 15, the sheath 66 is withdrawn by moving same in a generally proximal direction, and the stent 31 is released from the sheath 66. This release can be such that adjacent circumferential sections of the stent expand in a generally sequential manner, which is generally illustrated in FIG. 15.

After this procedure is completed, the entire stent 31 has been sprung, and it springingly engages the dilated lesion 61a, which is generally illustrated in FIG. 16. Thereafter, as seen in FIG. 17, the catheter 63 can be moved in a generally proximal direction until the balloon 67 is again generally aligned with the dilated lesion 61a, as desired. Then, the balloon 67 can be pressurized in order to further implant the stent 31 and in order to further dilate the lesion as desired so as to form a treated lesion 61b which remains after the catheter 63 is removed, as is generally shown in FIG. 18.

FIGS. 19 through 23 show an arrangement that is especially suitable for non-elastic stents in which the expandable segments thereof are made of malleable material. With reference to FIGS. 19 and 20, a stenosis or lesion 61 within blood vessel 62 is transluminally reached by a balloon catheter 71 having a stent 31 overlying the collapsed balloon 72 of the catheter 71. The balloon 72 is then expanded in a well-known manner, at which time the stent 31 is also expanded by opening the expandable segments thereof. An intermediate dilation position is shown in FIG. 21, and an initially dilated lesion 61a is shown therein. FIG. 22 shows additional dilation by the balloon 72, and the thus treated lesion 61b is also shown. After this stage is achieved, the balloon catheter 71 is removed, as shown in FIG. 23.

The stent 31 remains in place as generally illustrated in FIG. 23 because the malleable material (or for that matter an elastic material) exerts a hoop stress when it is expanded to the size illustrated in FIG. 23 such that it will not collapse by inwardly directed radial forces presented by the treated lesion and vessel wall or the like. In other words, the hoop stress of the expanded stent is greater than the hoop forces exerted by the passageway within which the stent is implanted. In addition, the force required to open the collapsed stent by the balloon is less than the hoop force provided by the balloon. In other words, the hoop stress of the collapsed or unextended stent is less than that of the hoop force provided by the pressurized balloon of the catheter. One feature that can contribute to the advantageous hoop stress properties of the malleable stents of the type illustrated in the drawings is the ability of the stent to expand well beyond that needed to effect the dilation procedure. For example, a typical dilation procedure and stent extension is one in which the fully extended dilating diameter or circumference is approximately three times the insertion or collapsed diameter or circumference. With stent structures such as those illustrated in the drawings, the amount of possible expansion can be on the order of two to twenty times, depending upon the length of each undulation and the distance between the legs. This feature, together with the malleability of the particular material utilized, tends to reduce the hoop force that is needed to expand the stent to about three times its insertion or collapsed configuration.

FIGS. 24 and 25 illustrate a stent withdrawal procedure and a snare catheter system that can be used to remove or explant implanted stents according to the present invention. A snare catheter, generally designated as 74, is illustrated. An elongated member 75 is slidably positioned within a catheter body 76. Elongated member 75 includes a hook member 77 at its distal end. When extended into the stent 31, the hook member 77 snares a portion of the stent 31. A suitable control structure, such as the puller assembly 78 illustrated is manipulated in order that the hook member moves in a proximal direction, with the result that the stent begins to uncoil and is opened to such an extent that it can be passed through the blood vessel 62 or the like until it is totally removed from the body by continued movement of the elongated member 75 in the proximal direction.

For purposes of illustration, the following details are given regarding a typical stent 31. An exemplary malleable material is tantalum wire having a diameter of 0.005 inch wound on a mandrel having a nominal diameter of 0.020 inch. The length of each leg 46 is on the order of about 0.048 inch, and the center-to-center spacing between adjacent integral or living hinges 36 is about 0.010 inch. A typical collapsed or insertion outer diameter for such a stent is about 0.085 inch, with the inner diameter thereof being about 0.075 inch. The overall length of the stent 31 is selected to be that generally needed to treat the lesion or the like inasmuch as the overall length of the stent will remain substantially the same whether it is collapsed or extended, except to the degree that the legs 46 of the exterior circumferential sections 32 move somewhat inwardly as the hinge is flexed, thereby somewhat nominally decreasing the overall length of the stent. A typical expanded diameter is 0.240 inch outside diameter with 0.230 inch inside diameter. The expansion ratio is approximately 2.8 in this representative device.

It will be understood that the embodiments of the present invention which have been described are illustrative of some of the applications of the principles of the present invention. Numerous modifications may be made by those skilled in the art without departing from the true spirit and scope of the invention.

I claim:

1. A radially expandable endoprosthesis, comprising:
   a plurality of generally circumferential sections, including end and intermediate generally circumferential sections, said end and intermediate generally circumferential sections being substantially adjacent to one another and generally parallel to each other in order to thereby generally defined an endoprosthesis having a longitudinal axis along which each of said generally circumferential sections are axially spaced;
   each of said generally circumferential sections includes an expandable segment that imparts radial expandability to said generally circumferential section whereby said section has an unexpanded insertion circumference and an expanded implantation circumference which is greater than said unexpanded insertion circumference;
   said expandable segment of each generally circumferential section is a generally foldable member that is bendable between a generally closed orientation and a generally opened orientation so as to impart radial expandability to the generally circumferential section;
   said generally circumferential sections form a continuous helix that defines an axially extending endoprosthesis; wherein said end sections each include a free end; and
   means for engaging the free end of each of said end sections with an adjacent one of said intermediate generally circumferential sections, thereby avoiding the presentation of loose ends on the endoprosthesis.

2. The endoprosthesis according to claim 1, wherein said foldable member includes a generally elbow-like member.

3. The endoprosthesis according to claim 1, wherein said foldable member includes a pair of legs unitarily connected together at a bendable portion.

4. The endoprosthesis according to claim 1, wherein said generally circumferential sections form a substantially cylindrical endoprosthesis.

5. The endoprosthesis according to claim 1, wherein said expandable segment is a malleable member, and wherein the expanded implantation circumference is achieved by radially directed forces from an expandable element of a catheter.

6. The endoprosthesis according to claim 1, wherein each of said generally foldable members has a pair of legs joined by a substantially U-shaped portion, and alternating ones of said substantially U-shaped portions are substantially oppositely oriented.

7. The endoprosthesis according to claim 1, wherein said generally foldable member is substantially V-shaped.

8. The endoprosthesis according to claim 1, wherein each of said generally foldable members has a pair of legs joined by a substantially V-shaped portion, and alternating ones of said substantially V-shaped portions are substantially oppositely oriented.

9. The endoprosthesis according to claim 1, wherein said endoprosthesis is generally tubular, and respective circumferential edges of respective generally circumferential sections are generally adjacent to each other.

10. The endoprosthesis according to claim 1, wherein said expandable segment of each generally circumferential section had been formed by winding a strand on a shaped mandrel to form a wound strand which was subsequently flattened to a generally uni-planar configuration, and wherein said generally uni-planar wound strand was subsequently wrapped around another mandrel and removed therefrom to thereby provide said radially expandable endoprosthesis.

11. The endoprosthesis according to claim 1, wherein each of said generally foldable members has a pair of legs joined at substantially right angles at opposite ends of a substantially straight section in order to thereby define generally right-angled zig-zag structure.

12. A radially expandable endoprosthesis, comprising:
    a plurality of generally circumferential sections, including end and intermediate generally circumferential sections, said end and intermediate generally circumferential sections being substantially adjacent to one another and generally parallel to each other in order to thereby generally define an endoprosthesis having a longitudinal axis along which each of said generally circumferential sections are axially spaced;
    each of said generally circumferential sections includes an expandable segment that imparts radial expandability to said generally circumferential section whereby said section has an unexpanded insertion circumference and an expanded implantation circumference which is greater than said unexpanded insertion circumference;
    said expandable segment of each generally circumferential section is a generally foldable member that is bendable between a generally closed orientation and a generally opened orientation so as to impart expandability to the generally circumferential section;
    said generally circumferential sections form a continuous helix that defines an axially extending endoprosthesis; wherein said end sections each have a free end; and
    hook means for engaging the free end of each of said end portions to an adjacent one of said intermediate generally circumferential sections, thereby avoiding the presentation of loose ends on the endoprosthesis.

13. The endoprosthesis according to claim 12, wherein said generally foldable member is substantially U-shaped.

14. A radially expandable endoprosthesis assembly, comprising:
- a plurality of generally circumferential sections, including end and intermediate generally circumferential sections, said end and intermediate generally circumferential sections being substantially adjacent to one another and generally parallel to each other in order to thereby generally define an endoprosthesis having a longitudinal axis along which each of said generally circumferential sections are axially spaced;
- each of said generally circumferential sections includes an expandable segment that imparts radial expandability to said generally circumferential section whereby said section has an unexpanded insertion circumference and an expanded implantation circumference which is greater than said unexpanded insertion circumference;
- said expandable segment of each generally circumferential section is a generally foldable elastic spring-like member that is bendable between a generally closed orientation and a generally opened orientation so as to impart radial expandability to the generally circumferential section;
- said generally circumferential sections form a continuous helix that defines an axially extending endoprosthesis; wherein said end section each have a free end; and
- means for engaging the free end of each of said end sections with an adjacent one of said intermediate generally circumferential sections, thereby avoiding loose ends on the endoprosthesis; and
- further including overlying sheath means for maintaining the unexpanded insertion circumference of the endoprosthesis in opposition to outwardly directed generally radial forces imparted by said elastic spring-like member onto an inside surface of the sheath means until said spring-like member is removed from the sheath to obtain said expanded implantation circumference.

15. An implantable and explantable endoprosthesis system, comprising a radially expandable axially extending endoprosthesis and a device for transluminally explanting the endoprosthesis; said endoprosthesis includes:
- a plurality of generally circumferential sections, including end and intermediate generally circumferential sections being substantially adjacent to one another and generally parallel to each other in order to thereby generally define an endoprosthesis having a longitudinal axis along which each of said generally circumferential sections are axially spaced,
- each of said generally circumferential sections includes an expandable segment that imparts radial expandability to said generally circumferential section whereby said section has an unexpanded insertion circumference and an expanded implantation circumference which is greater than said unexpanded insertion circumference,
- said expandable segment of each generally circumferential section is a generally foldable member that is bendable between a generally closed orientation and a generally opened orientation so as to impart expandability to the generally circumferential section,
- said generally circumferential sections form a continuous helix that defines an axially extending endoprosthesis; wherein said end sections each have a free end;
- means for engaging the free end of each of said end sections with an adjacent one of said intermediate generally circumferential sections, thereby avoiding loose ends on the endoprosthesis; and
- said device for transluminally explanting the endoprosthesis includes:
- a catheter member that is percutaneously insertable into a blood vessel or the like within which said endoprosthesis has been radially expanded and implanted,
- an elongated member slidably mounted within said catheter member, said elongated member having a proximal portion exterior of the body,
- snaring means at a distal end of the elongated member, said snaring means having a size whereby it slidably passes through said catheter member,
- means for manipulating a proximal portion of the elongated member from a location exterior of the body, said manipulating means facilitating engagement of said snaring means with one of said circumferential sections of the implanted endoprosthesis,
- puller means for sliding the elongated member and the snaring means in a proximal direction within said catheter member by moving the body-exterior proximal portion of the elongated member in a direction away from the endoprosthesis, and
- said puller means further being for at least partially uncoiling said helix and for reducing the radial size of the endoprosthesis to less than said expanded implantation circumference and such that it will pass through the catheter member and from the body, whereby the endoprosthesis of reduced radial size has been fully explanted.

16. The system according to claim 15, wherein each of said generally foldable members has a pair of legs and a foldable portion, and alternating ones of said foldable portions are substantially oppositely oriented.

17. The system according to claim 1, wherein said foldable member of the endoprosthesis includes a generally elbow-like member.

18. The system according to claim 15, wherein said foldable member of the endoprosthesis includes a pair of legs unitarily connected together at a bendable portion.

19. The system according to claim 15, wherein said expandable segment of the generally circumferential section of the endoprosthesis had been formed by winding a strand on a shaped mandrel to form a wound strand, said wound strand having been subsequently flattened, and said circumferential section is defined by said flattened wound strand in that said flattened wound strand was subsequently wrapped around a mandrel and removed therefrom to thereby provide said radially expandable endoprosthesis.

20. An implantable and explantable endoprosthesis system, comprising a radially expandable axially extending endoprosthesis and a device for transluminally explanting the endoprosthesis; said endoprosthesis includes:
- a plurality of generally circumferential sections, including end and intermediate generally circumferential sections, said end and intermediate generally circumferential sections being substantially adjacent to one another and generally parallel to each other in order to thereby generally define an endoprosthesis having a longitudinal axis along which each of said generally circumferential sections are axially spaced, each of said generally circumferential sections includes an expandable segment that imparts radial expandability to said generally circumferential section whereby said section has an unexpanded insertion circumference and an expanded implantation circumference which is greater than said unexpanded insertion circumference, said expandable segment of each generally circumferential section is a generally foldable member that is bendable between a generally closed orientation and a generally opened orientation so as to impart radial expandability to the generally circumferential section, said generally circumferential sections form a continuous helix that defines an axially extending endoprosthesis; wherein said end sections each have a free end, and means for engaging the free end of each of said end sections with an adjacent one of said intermediate generally circumferential sections, thereby avoiding the presentation of loose ends on the endoprosthesis; and said device for transluminally explanting the endoprosthesis includes:

an elongated member that is percutaneously insertable into a blood vessel or the like within which said endoprosthesis has been radially expanded and implanted, said elongated member having a proximal portion exterior of the body, snaring means at a distal end of the elongated member, means for manipulating a proximal portion of the elongated member from a location exterior of the body, said manipulating means facilitating engagement of said snaring means with one of said circumferential sections of the implanted endoprosthesis, puller means for sliding the elongated member in a proximal direction by moving the body-exterior proximal portion of the elongated member in a direction away from the endoprosthesis, said puller means further being for at least partially uncoiling said helix and for reducing the radial size of the endoprosthesis to less than said expanded implantation circumference and such that said endoprosthesis will pass through the blood vessel or the like, and means for completely removing the elongated member from the body until the endoprosthesis of reduced radial size has been fully explanted.

* * * * *

UNITED STATES PATENT AND TRADEMARK OFFICE
CERTIFICATE OF CORRECTION

PATENT NO. : 5,019,090

DATED : May 28, 1991

INVENTOR(S) : Leonard Pinchuk

It is certified that error appears in the above-identified patent and that said Letters Patent is hereby corrected as shown below:

Col. 5, line 14, "of" should read --or--.
    Col. 9, line 29, "defined" should read --define--.
    Col. 11, line 27, "section" should read --sections--; line 48, after "sections" insert --; said end and intermediate generally circumferential sections--.
    Col. 12, line 41, "1," should read --15,--.

Signed and Sealed this

Second Day of November, 1993

*Attest:*

BRUCE LEHMAN

*Attesting Officer*     Commissioner of Patents and Trademarks